United States Patent
Reich et al.

(10) Patent No.: US 8,911,431 B2
(45) Date of Patent: Dec. 16, 2014

(54) OPHTHALMOLOGICAL LASER SYSTEM AND OPERATING METHOD

(75) Inventors: Matthias Reich, Jena (DE); Dieter Grebner, Grossloebichau (DE); Andreas Koch, Jena (DE); Juergen Ledermann, Jena (DE); Manfred Dick, Gefell (DE); Marco Hanft, Jena (DE)

(73) Assignee: Carl Zeiss Meditec AG, Jena (DE)

(*) Notice: Subject to any disclaimer, the term of this patent is extended or adjusted under 35 U.S.C. 154(b) by 149 days.

(21) Appl. No.: 12/996,250

(22) PCT Filed: Jun. 4, 2009

(86) PCT No.: PCT/EP2009/003980
§ 371 (c)(1),
(2), (4) Date: Jun. 16, 2011

(87) PCT Pub. No.: WO2009/146906
PCT Pub. Date: Dec. 10, 2009

(65) Prior Publication Data
US 2011/0264081 A1    Oct. 27, 2011

(30) Foreign Application Priority Data
Jun. 5, 2008  (DE) .................... 10 2008 027 358

(51) Int. Cl.
*A61F 9/008* (2006.01)
*A61B 3/10* (2006.01)
*A61B 3/117* (2006.01)

(52) U.S. Cl.
CPC ............... *A61F 9/008* (2013.01); *A61B 3/1173* (2013.01); *A61F 9/00838* (2013.01); *A61F 2009/0087* (2013.01)
USPC ....................................... 606/4; 606/5; 606/6

(58) Field of Classification Search
CPC .................. A61F 9/008; A61F 9/0838; A61F 2009/0087; A61B 3/1173
USPC .......................................... 606/107, 166, 4–6
See application file for complete search history.

(56) References Cited

U.S. PATENT DOCUMENTS

| 5,672,881 A | * | 9/1997 | Striepeke et al. | .......... 250/461.2 |
| 6,112,114 A | * | 8/2000 | Dreher | .......... 600/476 |

(Continued)

FOREIGN PATENT DOCUMENTS

| EP | 0 983 757 A2 | 3/2000 |
| EP | 0983757 A2 * | 3/2000 |

(Continued)

OTHER PUBLICATIONS

Dhaliwal et al., Abstract for "Corneal and external disorders", Current Opinion in Ophthalmology, 18(4):300-307, Jul. 2007.

(Continued)

*Primary Examiner* — Gary Jackson
*Assistant Examiner* — Boniface N Nganga
(74) *Attorney, Agent, or Firm* — Patterson Thuente Pedersen, P.A.

(57) ABSTRACT

A polarization beam splitter selectively decouples detection light onto a detector such that it has a polarization direction that differs from the emitted illumination light. This enables the detection of the light scattered back in the eye lens at a high level of accuracy, since stray light from reflections at optical components of the light path is suppressed. In the generating of photo disruptions or other incisions, the ray exposure of the retina may be reduced in that the incisions being furthest away from the laser are induced first such that laminar gas inclusions with an existence duration time of at least 5 seconds result. In this manner the laser radiation propagated in the direction of the retina in further incisions are scattered and partially reflected such that the influence impinging upon the retina is reduced.

21 Claims, 4 Drawing Sheets

(56) References Cited

U.S. PATENT DOCUMENTS

| | | | |
|---|---|---|---|
| 6,726,679 B1 | 4/2004 | Dick et al. | |
| 6,736,508 B2 * | 5/2004 | Xie et al. | 351/209 |
| 6,905,210 B2 | 6/2005 | Applegate et al. | |
| 2004/0119004 A1 * | 6/2004 | Wine et al. | 250/234 |
| 2004/0199149 A1 | 10/2004 | Myers et al. | |
| 2005/0107773 A1 * | 5/2005 | Bergt et al. | 606/4 |
| 2005/0243414 A1 * | 11/2005 | Masuyama | 359/387 |
| 2006/0195076 A1 * | 8/2006 | Blumenkranz et al. | 606/4 |
| 2006/0217688 A1 * | 9/2006 | Lai | 606/4 |
| 2007/0179483 A1 * | 8/2007 | Muhlhoff et al. | 606/10 |
| 2007/0185475 A1 | 8/2007 | Frey et al. | |
| 2007/0236699 A1 | 10/2007 | Chou et al. | |
| 2008/0077121 A1 * | 3/2008 | Rathjen | 606/5 |
| 2008/0078752 A1 * | 4/2008 | Bischoff et al. | 219/121.72 |
| 2010/0191230 A1 * | 7/2010 | Dick et al. | 606/5 |

FOREIGN PATENT DOCUMENTS

| | | |
|---|---|---|
| EP | 1212022 A1 | 6/2002 |
| WO | WO 99/44491 | 9/1999 |
| WO | WO 03/070090 A2 | 8/2003 |
| WO | WO 2005/070358 A1 | 8/2005 |
| WO | WO 2005/122875 A1 | 12/2005 |
| WO | WO 2006/074469 A2 | 7/2006 |
| WO | WO 2007/001486 A2 | 1/2007 |
| WO | WO 2007/084579 A2 | 7/2007 |
| WO | WO 2007/084602 A2 | 7/2007 |
| WO | WO 2007/084627 A2 | 7/2007 |
| WO | WO 2007/084694 A2 | 7/2007 |
| WO | WO 2007084694 A2 * | 7/2007 |
| WO | WO 2008/017428 A2 | 2/2008 |
| WO | WO 2008017428 A2 * | 2/2008 |

OTHER PUBLICATIONS

Fisher, "The Mechanics of Accommodation in Relation to Presbyopia", Eye, 1988, vol. 2, pp. 646-649.

Krueger et al., "First safety study of femtosecond laser photodisruption in animal lenses: Tissue morphology and cataractogenesis", J Cataract Refract Surg, Dec. 2005, vol. 31, pp. 2386-2394.

Nikon C1, WiTec AFM attachment, Replacement of confocal aperture by point and ring detector. (Synonym: VAAS), prior to Jul. 2013, 1 page.

Wooten et al., "Using scotopic and photopic flicker to measure lens optical density", Ophthalmic and Physiological Optics, 2007, vol. 27, No. 4, pp. 321-328 (Abstract Only—1 page).

* cited by examiner

OPHTHALMOLOGICAL LASER SYSTEM AND OPERATING METHOD

PRIORITY CLAIM

The present application is a National Phase entry of PCT Application No. PCT/EP2009/003980, filed Jun. 4, 2009, which claims priority from German Application Number 102008027358.9, filed Jun. 5, 2008, the disclosures of which are hereby incorporated by reference herein in their entirety.

FIELD OF THE INVENTION

The invention relates to an ophthalmological laser system, particularly for analysis and/or therapy of a presbyopia, with a laser, the radiation of which is focusable in an examination region as illumination light via an illumination beam path, which exhibits a beam splitter, a scanner unit, and focusing optics, whereby radiation, which reaches the beam splitter from the direction of the examination region, reaches a detector as detection light through a confocal aperture diaphragm. Furthermore, the invention relates to an operating method for an ophthalmological laser system.

BACKGROUND

Accommodation is the ability of the eye to create a sharp image on the retina of an object located at any given distance. Thereto, the required adjustment of the refractive power occurs essentially through the elastic deformation of the lens. The possible maximum change in refractive power is called amplitude of accommodation. It can amount to 16 dioptors and decreases with age.

Presbyopia or age-related farsightedness, i.e., the reduced amplitude of accommodation of the eye lens, is the result of an age-related hardening and/or thickening of the eye lens. Typically, an eye lens is called presbyopic when its amplitude of accommodation drops below 3 dioptors. Presbyopia is not a pathological process but a natural consequence of old age, starting at age 40.

In ophthalmology it has been suggested to restore improved deformability of a hardened lens through suitable incisions or creation of bubbles by means of a refractive surgical therapy, particularly photodisruption or other incisions. Thereby, the accommodative capacity of the lens is to be partially regenerated.

Ophthalmological laser systems for presbyopia therapy have already been described in prior art. For example, WO 2008/017428 A2 discloses a navigation device for optical analysis and treatment of the inner structure of the eye lens.

The navigation device is equipped with a detection device and a treatment device, whereby the detection device can comprise a confocal detector and/or a confocal laser scanner. A photomultiplier (PMT) or an avalanche photodiode (APD) is suggested as detector. The same laser is provided for the analysis of the inner structure as well as treatment, whereby the detection beam path is coupled by means of a beam splitter into the treatment beam path. Thereby, the laser light, backscattered in the eye lens, is for analysis, in order to determine position, geometry, and structure of the eye lens. By means of the detected inner structure and the individual geometric form of the eye lens, the cut geometries to be produced during treatment are determined. For said purpose, a basic pattern is adjusted to the detected individual geometry.

A problem is that the intensity of the light backscattered in the eye lens is very low due to the inherent properties of the eye lens—for a high imaging quality, the scatter must be as slight as possible. As a result, the detection contains a relatively great number of flaws.

SUMMARY OF THE INVENTION

The invention is based on the task of improving an ophthalmological laser system of the initially mentioned type in order to allow for the detection of the light backscattered in the eye lens with increased accuracy.

According to the invention, the beam splitter is a polarization beam splitter, which decouples the detection light on the detector in such a way that it exhibits a polarization direction different from the emitted illumination light.

A large portion of the light, which impinges on the beam splitter from the examination region, originates from reflections on the optical components of the beam path, e.g., the surfaces of the focusing optics; therefore, it exhibits the same polarization direction as the illumination light. Since the beam splitter only directs light as detection light to the detector with a different polarization direction, such stray light is suppressed. However, light backscattered in the eye lens exhibits an altered polarization direction. Therefore, when compared to prior art, the detection of the light backscattered in the eye lens is possible with greater accuracy.

It is possible to achieve an even greater signal strength, whereby an optical phase retardation system in the illumination beam path between the focusing optics and the examination region is arranged in such a way that the passing illumination light obtains a polarization direction corresponding to the decoupled detection light. As a result, the stray light exhibits the same polarization direction as the radiation from the laser, while the illumination light, which reaches the eye lens and is modified in the phase retardation system, obtains a defined, different polarization direction. Through the selection of the light of said polarization direction as detection light by means of the polarization beam splitter, only such light, which was backscattered in the eye lens, is detected almost exclusively. Stray light, which originates from reflections on optical components, is even more effectively kept away from the detector.

In one embodiment, the laser system exhibits a control unit, which three-dimensionally scans an eye lens, arranged in the examination region, by means of the laser at illumination laser power, whereby it irradiates the lens at various points and detects by means of the detector in the form of detection light from said points and subsequently determines a form and/or structure and/or position of the eye lens by means of the detection light. As a result, the form and/or structure and/or position of the eye lens can be determined with great accuracy.

Aside from the position of the lens, the location of the eye lens also comprises, according to the invention, its spatial orientation. The information regarding the orientation can also be contained in the form of the eye lens.

The structure describes the inner configuration of the lens, e.g., inclusions or localized alterations, for example, from age-related tissue modifications or a previous presbyopia therapy.

In an example embodiment, the control unit subtracts a darkfield value from the mapped detection light. This can either be a mutual darkfield value for all scan points or several point-specific darkfield values. This embodiment allows for a greater accuracy of the imaging of the light backscattered in the eye lens.

Advantageously, for the determination of form and/or position of the eye lens, the control unit identifies one or both boundary layers of the lens. By means of the drop in backscatter intensity between the anterior and posterior boundary layer, the boundary layers, and therefore the form and/or position of the lens, can be determined with great accuracy. Alternatively or additionally, an image recognition algorithm can be utilized for identification. It is also possible to have the boundary layers determined manually by operation personnel. Furthermore, tissue structures can advantageously be identified within the lens. For example, the core area (nucleus) and/or the periphery (cortex) can be detected.

In an example embodiment, the boundary layers are identified, whereby an increase of an intensity of the detection light between a first focal depth and a second focal depth and a decrease of the intensity of the detection light between a third focal depth and a fourth focal depth are determined. The anterior and posterior boundary layer are characterized in that the backscatter during focusing of a scan point in the boundary layer is significantly higher than during focusing of scan points outside or inside of the lens. Therefore, the boundary layers can be identified with little effort by determining an increase or decrease of the intensity of the detection light.

In an example embodiment, the radiation of the laser can, in addition to illumination laser power, be adjusted to a refractive surgical therapy laser power. As a result, the same laser can be utilized for the illumination during determination of form/structure/position of the lens as well as for therapy.

In said example embodiment, the control unit, after determining form and/or structure and/or position of the eye lens, preferably determines the irradiation control data for a refractive surgical therapy of the eye lens, whereby it adjusts a basic pattern of the eye lens to the determined form and/or position of the eye lens and irradiates the eye lens with a refractive surgical therapy laser power in accordance with the determined irradiation control data. Therefore, analysis of form/structure/position, and therapy form a direct unit. As a result, therapy is possible with great accuracy since errors due to a movement of the eye lens or the patient can be minimized.

Expediently, the control unit immobilizes an eye containing the eye lens before irradiation with illumination laser power by means of an immobilization device and releases the immobilization after the determination of the form and/or structure and/or position of the eye lens or after surgical treatment. As a result, the possible changes in the position of the lens through the patient are minimized, which increases the accuracy of the analysis and, as the case may be, therapy.

According to the invention, for the operating method for an ophthalmological laser system, the laser of which is switchable between an illumination laser power and a therapy laser power, and the laser light of which is focusable three-dimensionally variable in an eye lens, the following steps to be executed are provided: Immobilization of an eye containing the eye lens by means of an immobilization device; irradiation of an eye lens, positioned in the examination region, by means of the laser with illumination laser power and detecting of detection light by means of a detector, whereby the eye lens is scanned three-dimensionally through irradiating the eye lens at several points and mapping of detection light; determination of form and/or structure and/or position of the eye lens by means of the detection light at the scan points; determination of irradiation control data for a refractive surgical therapy, whereby a basic pattern of the eye lens is adjusted to the determined form and/or position of the eye lens; irradiation of the eye lens by means of the laser with a refractive surgical therapy laser power in accordance with the determined irradiation control data; release of the immobilization of the eye.

Contrary to refractive surgery on the cornea, it is impossible to immobilize the eye lens. Only the eye as a whole can be immobilized. The operating method, according to the invention, solves said problem, whereby, at first, the eye as a whole is immobilized and the actual form/structure/position of the lens is subsequently determined. Since the therapy step follows immediately thereafter and both steps can be completed in a short period of time, form/structure/position of the lens for determining the irradiation control data are immediately applied in the therapy step, rendering an immobilization of the lens unnecessary. However, for the therapy, a very high accuracy is nevertheless possible.

In other example embodiments of the laser system, a lock-in amplifier, coupled with the laser, is provided for the detector. This allows for the mapping of the detector signals with great accuracy, so that a possible therapy can also be executed with great accuracy.

In another example embodiment, the scanning process is effected in such a way that two consecutive scan points differ from each other in all three spatial coordinates. Through this type of scanning, a representative model of the eye lens with regard to form/structure/position can be obtained in a short period of time. This allows for decreasing the inaccuracy caused by movements of the lens by the patient. A control of the scanners in the form of a sine function is technically particularly advantageous. Controlling the x-y scanners in such a way that one of the scanners is controlled with exactly double the frequency than that of the other scanner results in a Lissajous figure, which resembles the figure eight.

A pulse frequency of the laser light, depending on the motion speed of a focal point of the laser beam relative to the eye lens, may be chosen. As a result, the radiation exposure of the lens and the eye overall can be decreased during analysis and/or particularly during therapy.

An additional aspect of the invention relates to the reduction of the radiation exposure of the retina during the generation of photodisruptions or other incisions. At first, according to the invention, one or several extensive incisions in the rearward section of the eye lens 2 are executed in such a way that extensive gas pockets are produced, which remain in place for at least 5 seconds. Said gas pockets or bubbles can be purposefully produced through a suitable selection of laser parameters, particularly the distance between the irradiation points and the laser energy. Due to said extensive gas pockets, the laser radiation, which propagates in the direction of the retina during the subsequent generation of further incisions in the anterior part of the eye lens 2, is scattered and partially reflected, resulting in a reduction of the energy per area (fluence) impinging on the retina.

In the following, the invention shall be further explained by means of embodiment examples.

BRIEF DESCRIPTION OF THE DRAWINGS

It is shown in.

DETAILED DESCRIPTION

Figure 1:
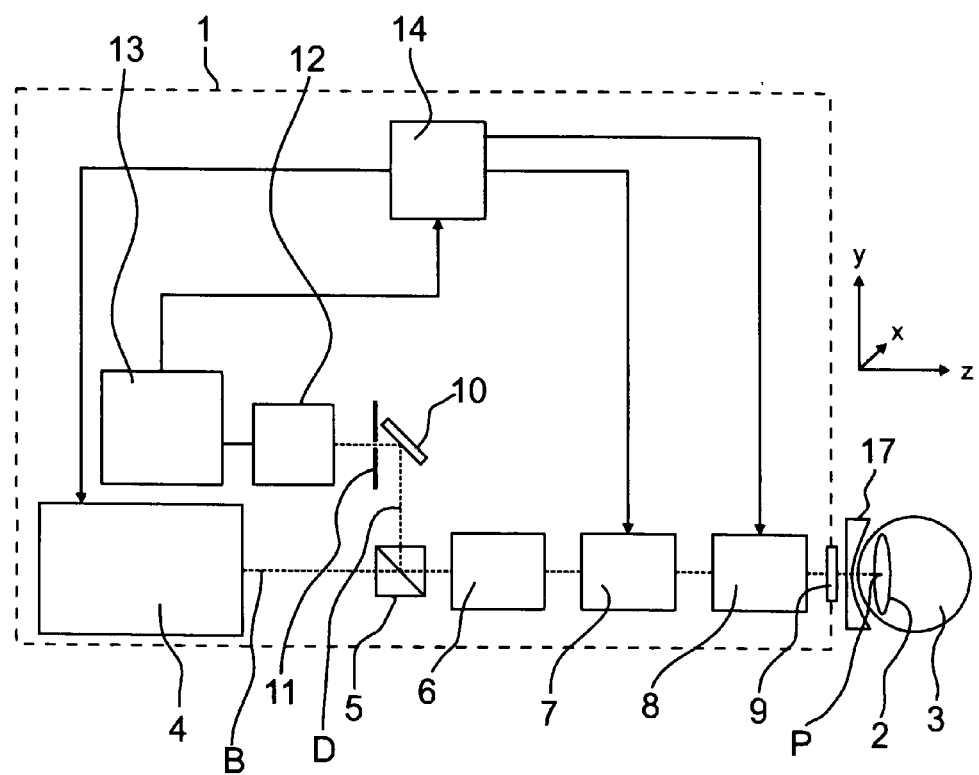
FIG. 1 is an ophthalmological laser system for the analysis of the eye lens.

FIG. 1 shows an exemplary ophthalmological laser system 1 for the analysis of a presbyopia of an eye lens 2 of an eye 3.

The laser system 1 comprises a laser 4, a polarization beam splitter 5, scan optics 6, a scanner unit 7, focusing optics 8, and an optical phase retardation system 9, which together form an illumination beam path B; as well as a deflection mirror 10, a confocal aperture diaphragm 11, and a detector 12, which form a decoupled detection beam path D; and an amplifier 13 and a control unit 14.

Between the laser system 1 and the eye 3, a contact glass 17 with an immobilization device for the eye 3 is positioned, behind which lies the examination region. Other embodiments for the realization of the solution, according to the invention, are possible (not depicted).

For example, the laser 4 is designed as pulsed TiSa infrared laser with a pulse length between 100 fs and 1000 fs. It emits laser radiation at an eye-safe illumination laser power in the range of 100 mW. Then scanner unit 7 comprises, for example, a number of galvanometric mirrors for the deflection of the laser radiation in the x- and y-directions via the eye lens 2. The focusing of the laser radiation in z-direction along the optical axis is effected, e.g., through a movable lens or lens group within the scan optics 6 or the focusing optics 8, or alternatively through a movable tube lens (not depicted). The optical phase retardation system 9, for example, is designed as λ/4 plate, which forms a border of the laser system. The detector 12, e.g., is designed as photomultiplier or as APD since the light intensities to be mapped are low. The amplifier 13 is designed as lock-in amplifier and connected to the detector 12 as well as the laser 4.

The pulsed IR laser radiation emerges from the laser 4 and initially passes unchanged through the polarization beam splitter 5. Then it is focused via scan optics 6, scanner unit 7, and focusing optics 8 as illumination light on a scan point P in the eye lens 2. Said scan point P can be shifted by means of the scanner unit 7 and a movable lens or lens group within the scan optics 6 or the focusing optics 8 in x-, y-, or z-direction in the eye lens 2. Thereby, the optical phase retardation system 9 effects a defined change of the polarization direction of the illumination light passing through.

At the boundary layers G1, G1 of the eye lens 2 and the inhomogeneous layers of the eye lens (not depicted), a scattering/reflection of the IR radiation occurs, whereby the radiation is partially depolarized in the eye 3.

Backscattered/reflected light also impinges on the illumination beam path B and there returns all the way back to the polarization beam splitter 5. The radiation components with unchanged polarization status pass through the polarization beam splitter 5 onto the laser 4. This refers particularly to reflections which originate from the scan optics 6 or the focusing optics 8. Such radiation components, which, after passing through the phase retardation system 9 and/or through depolarization in the eye 3, exhibit a changed polarization status in the eye lens 2, are deflected by the polarization beam splitter 5 as detection light into the detection beam path D to the detector 12. The detection light passes via a deflection mirror 10 through the confocal aperture diaphragm 11 onto the detector 12. In another embodiment, the deflection mirror 10 can be omitted or replaced by other beam guidance units. The confocal aperture 11 acts as discriminator in the z-direction, therefore, spatially resolved, only backscattered light is detected from a low focus volume. The control unit 14, through the deflection of the illumination light in x- and y-direction by means of the scanner unit 7 and change of the focusing in z-direction by means of the focusing optics 8, can irradiate random scan points P inside and outside of the eye lens 2 with illumination light and determine the strength of the backscatter at said points via the intensity of the corresponding detection light.

In order to determine information about form, structure, and position of the eye lens 2 with great accuracy in a short period of time, a suitable spatial distribution of points is scanned. From the hereby obtained values for the strength of the backscatter, form, inner structure, and position of the lens can be reconstructed. As a result, a presbyopia therapy can be performed patient-specific while taking the lens properties into account. In addition to presbyopia therapy, the laser system 1 can also be utilized in other ophthalmological applications, such as the diagnosis of the cornea, in order to gather information about the eye 3.

In the depicted embodiment, the optical phase retardation system 9 between the eye 3 and focusing optics 8 effects a defined rotation of the polarization direction of the passing illumination light, while reflected stray light, reflected at the optical components, initially maintains the original polarization direction.

As a result, the relative intensity of the detection light is increased since the polarization beam splitter 5 separates any light with deviating polarization direction as detection light. In alternative embodiments, the optical phase retardation system 9 can be omitted. Alternatively or additionally, additional polarizers (not depicted) can be positioned in the illumination and/or detection beam path in order to improve the signal quality. In another embodiment, the phase retardation system can be realized as depolarizer, so that the extent of the phase retardation varies via the beam profile.

Since the signals registered at the detector 12 exhibit a very low intensity, the electronic amplifier is adjusted to an optimized signal-to-noise ratio. Another example embodiment is the lock-in amplifier, which is temporally synchronized with the pulse generation and/or the repetition frequency of the laser 2. Other embodiments, for example, utilize so-called boxcar techniques or scanning techniques (sampling) with adding up or averaging. Advantageously, the entire amplifier system of the detector signal exhibits a nonlinear characteristic.

Figure 2A:
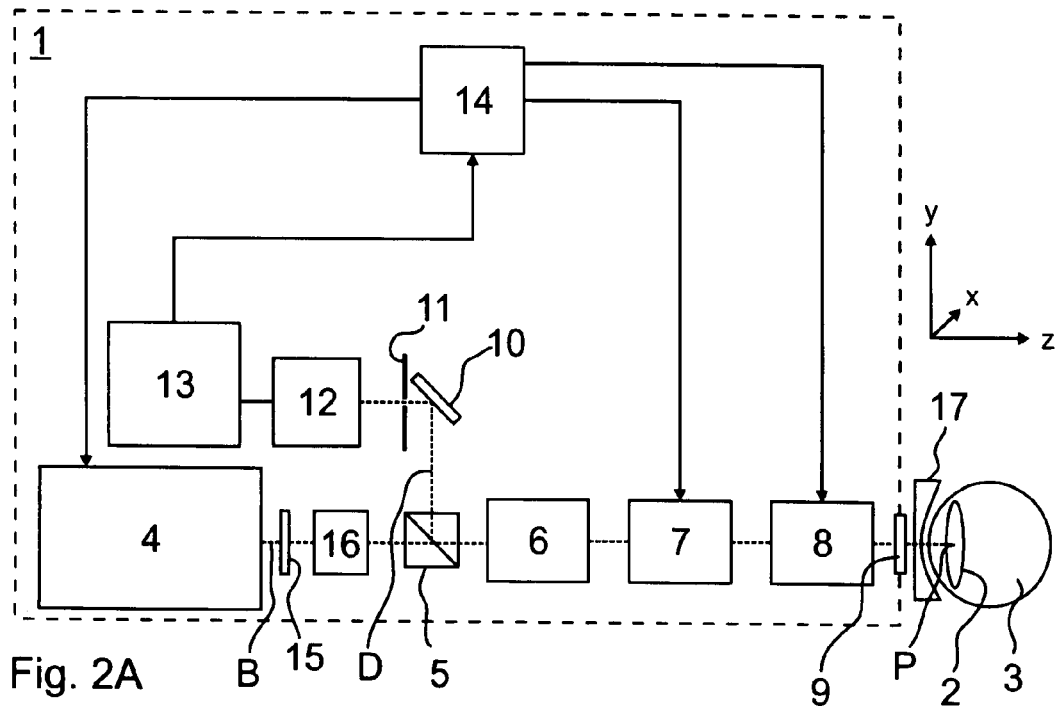
FIGS. 2A and 2B depict an ophthalmological laser system for the analysis and treatment of the eye lens.
Figure 2B:
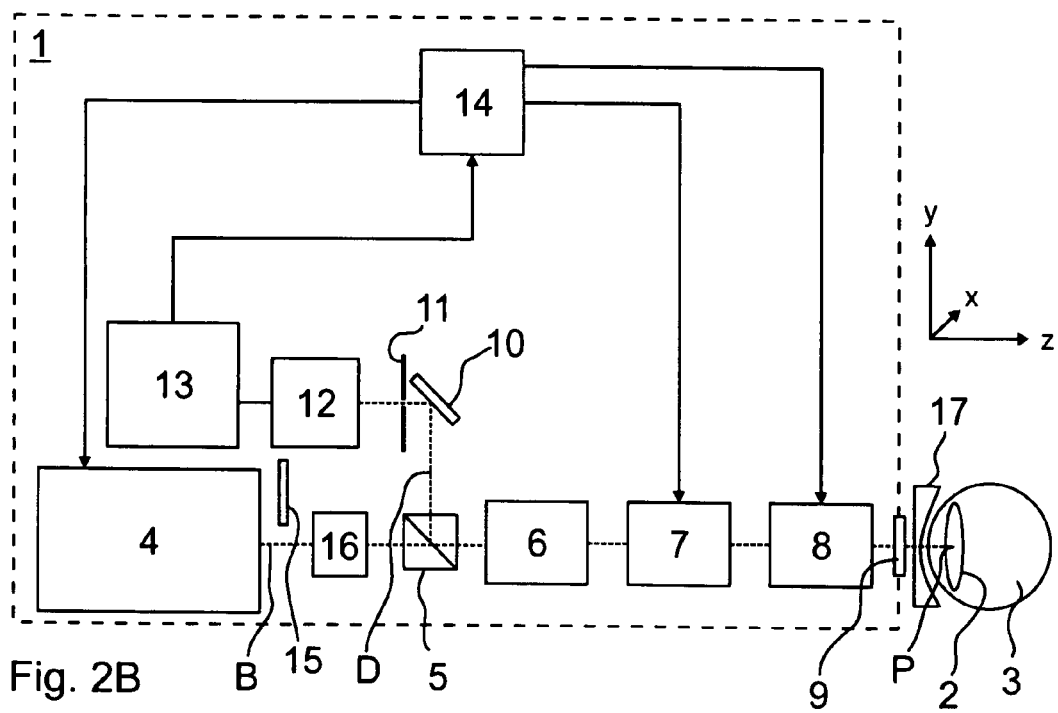

FIGS. 2A and 2B depict an ophthalmological laser system 1 for combined analysis and therapy of a presbyopia. It corresponds to a large extent with the laser system 1 in accordance with FIG. 1, but is additionally equipped with an attenuator 15, which can be tilted into the illumination beam path B, and a modulator 16, e.g., an acousto-optical modulator. The attenuator 15 is used for switching between an illumination laser power and therapy laser power. Illumination laser power is obtained through the attenuator 15, tilted into the illumination beam path B, and therapy laser power is obtained without the attenuator 15. The optical components, particularly optics 6 and 8, are optimized, corrected, and synchronized towards the goal of a best possible focus miniaturization. For example, its optical aberrations are minimized to a high degree, requiring only a low energy input for a photodisruption. The optical components are designed in such a way that the inherent dispersion of the intraocular media with regard to the change of pulse length as well as the inherent focusing effect of the gradient lens structure of the eye lens are pre-compensated.

As a result, the size of the focus volume can be maintained constant over the entire area of the eye lens and over its entire depth with an error variance of no more than 10%. Particularly, the focus volume can be shifted with a tolerance of +/−5 mm within a volume with a diameter of 7 mm and depth of 10 mm towards the apex of the cornea of the eye lens 2.

Figure 3:
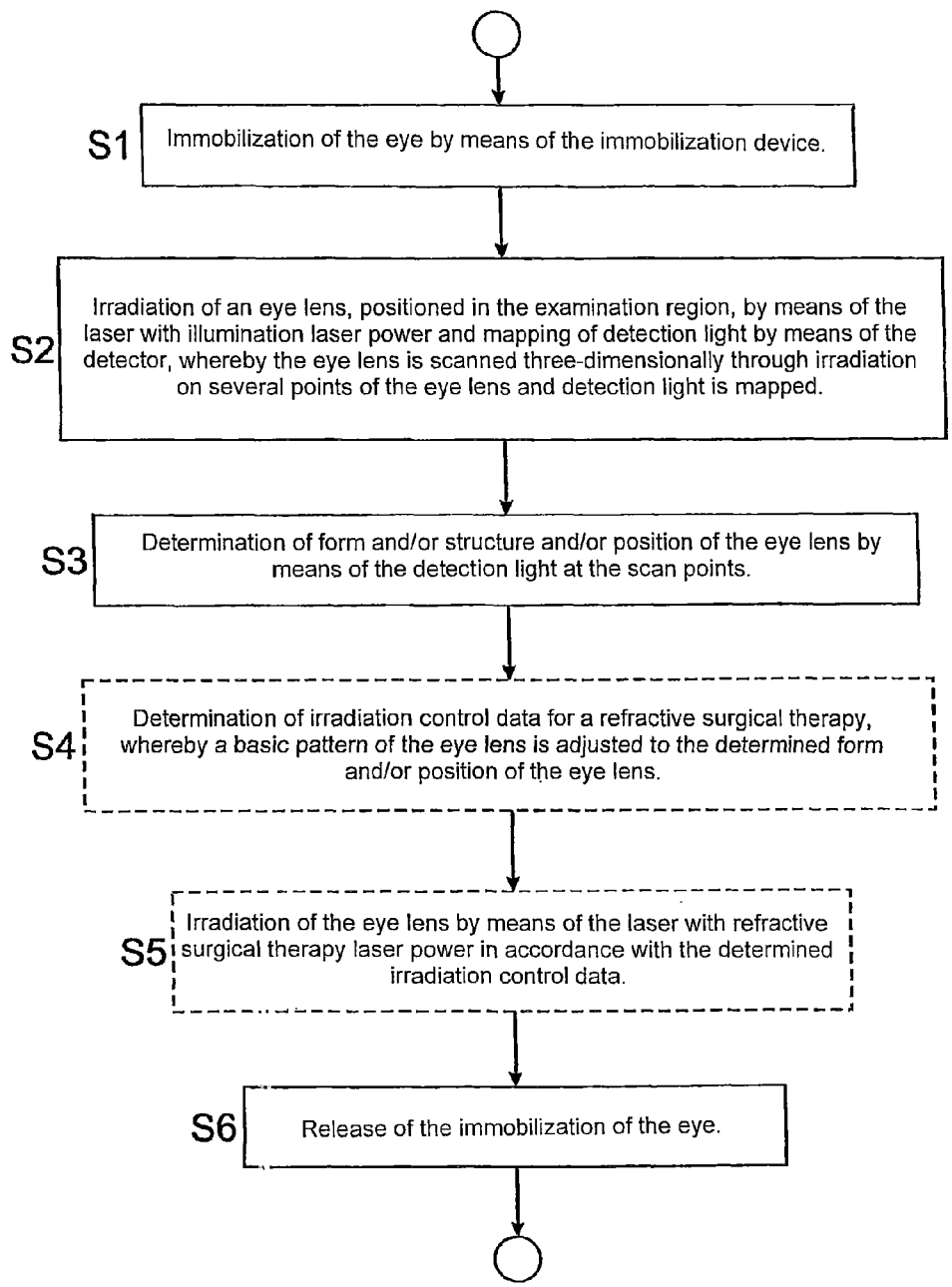
FIG. 3 is a flow diagram of an operating method.

The control unit 14 executes the operating method as shown in FIG. 3, whereby for an example pure analysis of the eye lens 2 only the solidly outlined steps S1, S2, S3, and S6 are executed. For an example presbyopia therapy all steps are executed. Thereby, the laser 4 is utilized not only for illumination during the detection phase but also for the treatment of the eye lens 2 during the immediately following therapy phase.

At first, the eye of the patient is immobilized, for example, secured to a contact glass device by means of a vacuum (step S1). In addition, the head of the patient can also be immobilized. Through a suitable target, the eye position of the patient can be kept as constant as possible. Thereby, an adjustable compensation of the angle between geometric and optical axis of the eye is possible.

The illumination light at illumination laser power is guided across the eye lens 2 along an adjustable, continuous, three-dimensional scan curve or structure, and detection light is mapped (step S2). Thereby, the pulse frequency, in dependence of the speed of the scan movement, is adjusted in such a way that a lower pulse frequency results from a slow scan movement than from a fast scan movement. The backscattered detection light is assigned sectionally or pointwise to individual points of the scan curve. Due to the continuity of the scan curve, consecutive scan points differ with regard to all spatial coordinates. From the detected signal values, respective darkfield values are advantageously subtracted, which are determined in a separate calibration phase.

From the intensities assigned to the scan points, form, structure, and the position of the eye lens 2 are reconstructed as model (step S3). Thereto, particularly its boundary layers can be identified, e.g., the anterior or posterior boundary layer and/or interior areas such as the junction between cortex and nucleus. For example, the model can represent the eye lens 2 as gradient lens, i.e., with an interior course of the refractive index of the lens medium. Particularly, the model can reproduce a tilting of the eye lens 2 towards the optical axis of the system 1.

Said information is used to adjust a basic pattern of the eye lens and the incisions, predefined by the operator beforehand, to the actual individual condition of the eye lens 2 in order to determine the irradiation control data by means of the adjusted basic pattern (step S4). For example, basic patterns can be spherical surfaces, ellipsoids, or conic sections, which are adjusted to the reconstructed model, e.g., through shifting, tilting, clipping of the boundaries, enlargement or stretching of the pattern in order to allow for a centering of the pattern with regard to the real position of the lens in space as well as an observance of safety zones. The irradiation control data comprise, e.g., control signals for the axes of the scanner unit and/or the internal z-focusing, and for the laser beam source and the power modulator 16.

Immediately thereafter, by means of the irradiation control data, the actual refractive surgical procedure is executed with therapy laser power (step S5). Thereby, for example, one or several photodisruption bubbles with a maximum pulse energy of preferably 0.5 µA are produced through the laser radiation at a pulse frequency from 100 kHz to 1 MHz and a pulse length of less than 1 ps, particularly 300 fs. Thereby, the radiation exposure of the retina can be reduced, whereby the therapy is initiated in the posterior area of the eye lens 2, e.g., with the rearmost incision, before executing additional therapeutic incisions in the central and anterior area of the eye lens 2. Lastly, the immobilization of the lens 2 is released (step S6).

Due to the identical beam path for analysis and therapy, the system 1 is self-calibrating. Since the irradiation control data are determined by means of the information about form/structure/position of the lens, obtained with the identical beam path, the therapy allows for great accuracy.

Through the use of adjusted scan curves (scan patterns), for example, in the form of Lissajous figures, the combined procedure can also be executed in a short period of time, for example, within a maximum of 30 seconds, which reduces inaccuracies due to movement and leads to better acceptance by the patient.

Figure 4:
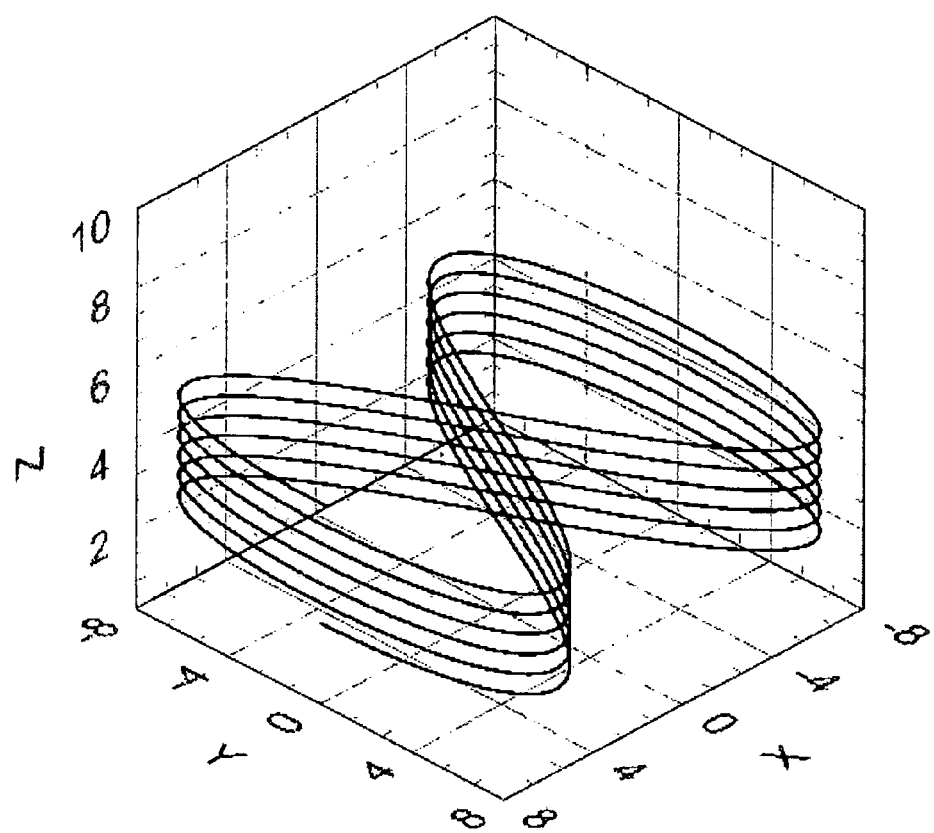
FIG. 4 is a space curve for the scanning of the eye lens;
In all drawings, all corresponding parts bear the same legend.

FIG. 4 shows an exemplary scan curve in the form of a spatially offset figure eight, which can be realized as a Lissajous figure by means of the scanner unit 6. It has the advantage of allowing for the determination of representative data for the reconstruction of a lens model with great accuracy in a short period of time.

Other exemplary forms of scanning and/or rastering can be (not depicted): two crossed rectangles in space; two cylindrical surfaces; a cylindrical body with a profile in the form of a FIG. 8 as depicted in FIG. 4; or several scans along one-dimensional lines. It is also possible to raster the volume of a cylinder or a cube. The volumes and/or surfaces can be scanned continuously or only partially, i.e., with gaps between the individual scan points. As a result, greater distances can occur between individual lines. The scanning structure stretches advantageously from the boundaries via an area from at least 2.5 mm up to 5 mm axially behind the contact glass and from at least 0 mm to 4 mm in diameter laterally with regard to the optical axis of the treatment optics.

The operating method, according to the invention, can also be utilized with other laser systems. For example, instead of the confocal detection, an interferometric measurement of the eye lens can be provided.

Legend
1 Ophthalmological laser system
2 Eye lens
3 Eye
4 Laser
5 Polarization beam splitter
6 Scan optics
7 Scanner unit
8 Focusing optics
9 Optical phase retardation system
10 Deflection mirror
11 Confocal aperture diaphragm
12 Detector
13 Amplifier
14 Control unit
15 Attenuator
16 Modulator
17 Contact glass
B Illumination beam path
D Detection beam path
P Scan point

The invention claimed is:

1. An ophthalmological laser system, for the diagnosis of an eye, a lens of the eye and/or therapy of presbyopia, the ophthalmological laser system comprising:
a laser emitting detection radiation, the radiation being selected to pass through a cornea and aqueous humor of the eye and being focusable in an examination region including the lens of the eye as illumination light via a beam path;
the beam path, comprising a beam splitter, a scanner unit, and focusing optics structured to focus the detection radiation in the examination region;
wherein returning detection radiation, which returns to the beam splitter from a direction of the examination region, reaches a detector as detection light through a confocal aperture diaphragm;

wherein the beam splitter is a polarization beam splitter, which decouples the detection light selectively onto the detector such that the detection light exhibits a polarization direction different from the illumination light; and a control unit programmed to control the scanner unit such that each two consecutive scan points of a continuous scan curve or structure differ from each other in all three spatial coordinates and to determine at least one of form, structure and position of an ocular structure based on the detection light returned from the scan points;

wherein the continuous scan curve or structure comprises a Lissajous pattern shape; and further wherein the control unit is further programmed to control the scanner unit such that the Lissajous pattern shape comprises two harmonics and wherein the two harmonics have different frequencies including a first frequency and a second frequency.

2. The ophthalmological laser system, according to claim 1, further comprising an optical phase retardation system positioned in the illumination beam path between the focusing optics and the examination region such that the passing illumination light is given a polarization direction which corresponds with the decoupled detection light.

3. The ophthalmological laser system, according to claim 1, wherein the control unit is programmed to execute the following:

irradiating of the lens of the eye, positioned in the examination region, by the laser with the illumination light at illumination laser power and mapping of detection light by the detector, directing the scanner unit to scan the eye lens three-dimensionally, irradiating the lens of the eye at several points; and mapping the detection light returned from the eye lens;

determining at least one of form, structure and position of the lens of the eye based on the detection light.

4. The ophthalmological laser system, according to claim 3, wherein the control unit is further programmed to subtract a darkfield value from the mapped detection light.

5. The ophthalmological laser system, according to claim 3, wherein the determining at least one of form, structure and position of the lens of the eye further includes identifying boundary layers of the lens.

6. The ophthalmological laser system, according to claim 3, wherein the radiation of the laser is, in addition to the illumination laser power, adjustable to a surgical therapy laser power.

7. The ophthalmological laser system, according to claim 6, wherein the control unit, after determining at least one of the form, the structure and the position of the lens of the eye, is further programmed to execute the following:

determining irradiation control data for a surgical therapy, wherein the control unit adjusts a basic pattern of the lens of the eye to at least one of the determined form and position of the lens of the eye; and irradiating the lens of the eye with a surgical therapy laser power in accordance with the determined irradiation control data.

8. The ophthalmological laser system, according to claim 7, wherein the control unit is further programmed to adjust a maximum pulse energy of 0.5 µJ for irradiation with therapy laser power.

9. The ophthalmological laser system, particularly according to claim 7, wherein the control unit determines the irradiation control data such that, first, an incision furthest from the laser is induced, wherein the incision is induced such that resulting extensive gas pockets remain in place for at least 5 seconds.

10. The ophthalmological laser system, according to claim 1, wherein the control unit is further programmed to immobilize an eye, containing the lens of the eye, before the irradiation with illumination laser power by application of an immobilization device, and after the determination of the at least one of the form, the structure and the position of the lens of the eye or after surgical therapy to release the immobilization of the eye.

11. The ophthalmological laser system, according to claim 1, further comprising a lock-in amplifier for the detector coupled with the laser.

12. The ophthalmological laser system, according to claim 1, wherein the laser comprises a pulsed laser and wherein at least one of the beam splitter, the scanner unit, and the focusing optics pre-compensate an inherent dispersion of intraocular media with regard to the pulse length and a self-focusing effect of a gradient lens structure of the lens of the eye.

13. The ophthalmological laser system, according to claim 1, wherein the first frequency is double the second frequency.

14. A computer implemented operating method for an ophthalmological laser system, the laser of which is switchable between an illumination laser power and a therapy laser power, and the laser light of which is focusable three-dimensionally variably in the lens of an eye, the method comprising:

immobilizing the eye containing the lens by application of an immobilization device;

irradiating the lens of the eye, positioned in the examination region with detection radiation, by application of the laser with an illumination laser power with laser radiation selected to pass through a cornea and aqueous humor of the eye;

scanning the laser focus of the detection radiation three-dimensionally in the lens thereby irradiating the lens at several scan points and such that each two consecutive scan points of a continuous scan curve or structure differ from each other in all three spatial coordinates such that the continuous scan curve or structure comprises a Lissajous pattern shape and such that the Lissajous pattern shape comprises two harmonics and the two harmonics have different frequencies including a first frequency and a second frequency;

mapping detection light returned from the scan points with a detector;

determining at least one of form, structure and position of the lens based on the detection light returned from the scan points;

determining irradiation control data for a surgical therapy, wherein a basic pattern of the lens is adjusted to the determined at least one of the form, structure and position of the lens;

irradiating the lens by application of the laser with a surgical therapy laser power in accordance with the determined irradiation control data; and releasing the immobilization of the eye.

15. The operating method, according to claim 14, further comprising adjusting a pulse frequency of the laser light, dependent on the speed of scan movement of a focal point of the laser beam relative to the lens.

16. The operating method, according to claim 14, further comprising subtracting a darkfield value from the mapped detection light.

17. The operating method, according to claim 14, further comprising identifying boundary layers of the lens for the determination of the at least one of the form or the position of the lens.

18. The operating method, according to claim 17, further comprising identifying the boundary layers by determining an increase of an intensity of the detection light between a first focal depth and a second focal depth and a decrease of the intensity of the detection light between a third focal depth and a fourth focal depth.

19. The operating method according to claim 14, further comprising utilizing a maximum pulse energy of 0.5 µJ for irradiation with therapy laser power.

20. The operating method according to claim 14, further comprising determining irradiation control data such that, first, an incision furthest from the laser is induced, wherein said incision is induced such that the resulting extensive gas pockets remain in place for at least 5 seconds.

21. The operating method, according to claim 14, further comprising scanning such that the first frequency is double the second frequency.

* * * * *